United States Patent [19]

Nicolson et al.

[11] Patent Number: 5,262,403
[45] Date of Patent: Nov. 16, 1993

[54] GLYCOSAMINOGLYCAN DERIVATIVES AND THEIR USE AS INHIBITORS OF TUMOR INVASIVENESS OF METASTATIC PROFUSION-II

[75] Inventors: Garth L. Nicolson, Kingwood, Tex.; Tatsuro Irimura, Tokyo; Motowo Nakajima, Kamagaya, both of Japan

[73] Assignee: Board of Regents, The University of Texas System, Austin, Tex.

[21] Appl. No.: 550,827

[22] Filed: Jul. 10, 1990

Related U.S. Application Data

[63] Continuation-in-part of Ser. No. 342,627, Apr. 8, 1989, abandoned, which is a continuation of Ser. No. 899,511, Aug. 21, 1986, abandoned, and a continuation-in-part of Ser. No. 839,890, Mar. 7, 1986, abandoned.

[51] Int. Cl.$^5$ .................. A61K 31/725; C08B 37/10
[52] U.S. Cl. ........................................ 514/56; 514/54; 536/21
[58] Field of Search .................. 514/45, 56; 536/21

[56] References Cited

U.S. PATENT DOCUMENTS

| | | |
|---|---|---|
| 2,727,889 | 12/1955 | Alburn . |
| 2,755,275 | 7/1956 | Cushing et al. . |
| 2,831,851 | 4/1958 | Vogler . |
| 3,118,816 | 1/1964 | Cushing . |
| 4,727,063 | 2/1988 | Naggi et al. . |
| 4,882,318 | 11/1989 | Vlodavsky et al. .................. 536/21 |

FOREIGN PATENT DOCUMENTS

| | | |
|---|---|---|
| 116801 | 8/1984 | European Pat. Off. . |
| 0140781 | 5/1985 | European Pat. Off. . |
| 0176769 | 8/1985 | European Pat. Off. . |
| 6117 | 5/1986 | Japan . |
| 1501098 | 2/1978 | United Kingdom . |
| WO88/01280 | 2/1988 | World Int. Prop. O. . |

OTHER PUBLICATIONS

Rong et al., Cancer, 57:586–590 (1986).
Nakajima et al., *Cancer Metastasis: Experimental and Clinical Strategies*, Welch et al. Eds., Alan R. Liss, New York, 113–122 (1986).
Folkman, *Important Advance in Oncology*, de Vita et al. Eds., J. B. Lippincott, Philadelphia, 42–62 (1985).
Castellot et al., J. Cell Physiol, 120:315–320 (1984).
Hilgard, *Cancer Invasion and Metastasis: Biologic and Therapeutic Aspects*, Nicolson et al. Eds., Raven Press, New York, 353–360 (1984).
Folkman et al., *Science*, 221:719–725 (1983).

(List continued on next page.)

Primary Examiner—Jacqueline Stone
Attorney, Agent, or Firm—Arnold, White & Durkee

[57] ABSTRACT

The present invention comprises a method for impeding the formation of tumor metastasis or tumor invasiveness in a host. Such inhibition comprises administration to the host of a glycosaminoglycan derivative substantially devoid of anticoagulation activity and is an effective inhibitory of heparanase activity. Such a glycosaminoglycan derivative may be provided by purchase or synthesis as directed herein. Parenteral administration to a tumor-bearing host of the glycosaminoglycan derivative results in the exposure of host-borne tumor cells thereto. Such exposure to effective levels of the derivative results in the inhibition of tumor heparanase activity and a lessening of invasiveness and metastatic spread.

Heparin, a glycosaminoglycan particularly effective as a heparanase inhibitor and an anti-clotting agent, is a preferred glycosaminoglycan for derivatization. Upon derivatization according to the present invention heparin may be converted into a glycosaminglycan derivative substantially devoid of anticoagulant activity but yet being an effective inhibitor of heparanase activity. Mere reduction of heparin carboxyl groups results in the production of a glycosaminoglycan derivative inhibitory to heparanase activity but without substantially anticoagulant activity non-anticoagulating, heparanase-inhibiting glycosaminoglycan derivatives may also be prepared from heparin, for example, by: at least partial N-desulfation and then N-acetylation; or N-, O-desulfation followed by N-resulfation.

11 Claims, 6 Drawing Sheets

OTHER PUBLICATIONS

Irimura et al., *Proc. Am. Soc. Cancer Res.*, 24:37, Abstract 144 (1983).
Nakajima et al., *J. Biol. Chem.*, 259:2283–2290 (1984).
Nakajima et al., *Science,* 220:611–613 (1983).
Irimura et al., *Anal. Biochem.*, 130:461–468 (1983).
Patent Cooperation Treaty International Application No. PCT/US91/04863 Search Report, Nov. 22, 1991.
Nicolson et al., *Invasion Metastasis,* 5:144–158 (1985).
Irimura et al., *Gann Monogr. Cancer Res.*, 29:35–46 (1983).
Fisher et al., NCI Monograph, 1:35–43 (1986).
Vlodavsky et al., *Cancer Res.*, 43:2704–2711 (1983).
Kramer et al., *J. Biol. Chem.*, 257:2678–2686 (1982).
Nicolson, *J. Hist. Cytochem.*, 30:214–220 (1982).
Nicolson, Biochem. Biophys., Acta, 695:113–176 (1982).
Guyton et al., *Circulation Res.*, 46:625–634 (1980).
Hoover et al., *Circ. Res.*, 47:578–583 (1980).
Tsubura et al., *Gann Monograph on Cancer Research,* 20:147–161 (1977).
Suemasu, *Gann Monograph on Cancer Research,* 20:163–172 (1977).
Hilgard et al., *Eur. J. Cancer,* 12:755–762 (1976).
Ross et al., *Science,* 180:1332–1339 (1973).
Michaels, *Lancet,* 2:832–833 (1964).
Nicolson, *Exp. Cell Res.*, 150:3–22 (1984).
Oosta et al., *J. Biol. Chem.*, 257:11249–11255 (1982).
PCT Search Report for UTSC:043PCT.
Inoue et al., *Carbohydrate Res.*, 46:87–95 (1975).
Irimura et al., *J. Cellular Biochem.*, Suppl. 9A, Abstracts of the 14th Annual Meeting, Jan. 12–Feb. 6, 1985.
Irimua et al., *J. Cellular Biochem.*, Suppl. 10A, Abstracts of the 15th Annual Meeting, Jan. 20–Feb. 15, 1986, #A141.
Carr, Nature, 198:1104–1105 (1963).
Schirrmacher, Adv. Cancer Res., 43:1–73 (1985).
Oldberg et al., *Biochemistry,* 19:5755–5762 (1980).
Dialog Search Report.
Iverius, *Biochem. J.,* 124:677–683 (1971).
Kanwar et al., *J. Cell. Biol.,* 86:688–693 (1980).
Fransson et al., *J. Biol. Chem.,* 256:13044–13047 (1981).
Hook et al., *Anal. Biochem.,* 119:236–245 (1982).
Fransson et al., *Carbohydrate Res.,* 110:135–144 (1982).
Nakajima et al., *Cancer Letters,* 31:277–283 (1986).
Irimura et al., *Cancer Res.,* 41:3411–3418 (1981).
Nicolson et al., *Cancer Res.,* 45:331–336 (1985).
Johnson et al., *Cancer Treatment Rep.,* 69:821–824 (1985).
Nagasawa et al., *Metho. Carbohyd. Chem.,* 8:287–289 (1980a).
Nagasawa et al., *Metho. Carbohyd. Chem.,* 8:291–294 (1980b).
Cherniak et al., *J. Biol. Chem.,* 239:2986–2990 (1964).
Taylor et al., *Meth Carbohyd. Chem.* 7:149–171 (1976).
Cappeletti et al., *Anal. Biochem.,* 99:311–315 (1979).
Wang et al., *Eur. J. Biochem.,* 153:125–130 (1985).
Fukuda et al., *J. Biochem.,* 80:1223–1232 (1976).
Irimura et al., *Biochem.,* 20:560–566 (1981).
Neri et al., *J. Natl. Cancer Inst.,* 68:507–517 (1982).
Irimura et al., *Biochemistry,* 25:5322–5328 (1986).
Nakajima et al., *Anal. Biochem.,* 157:162–171 (1986).

ORIGIN —

H. CARBOXYL REDUCED
G. N-RESULFATED N-O-DESULFATED
F. N-ACETYLATED N-O-DESULFATED
E. N,O-DESULFATED
D. N-ACETYLATED N-DESULFATED
C. COMPLETELY N-DESULFATED
B. PARTIALLY N-DESULFATED
A. INTACT

GLYCOSAMINOGLYCAN DERIVATIVES AND THEIR USE AS INHIBITORS OF TUMOR INVASIVENESS OF METASTATIC PROFUSION-II

This application is a continuation-in-part of U.S. Ser. No. 342,627, Apr. 8, 1989 which was a continuation under 37 CFR 1.62 of U.S. Ser. No. 899,511, filed Aug. 21, 1986 and a continuation-in-part of U.S. Ser. No. 839,890 filed Mar. 7, 1986, all now abandoned and incorporating by reference herein.

BACKGROUND OF THE INVENTION

The present invention relates to glycosaminoglycan derivatives useful in the inhibition of endoglycosidase activity and of tumor invasiveness or metastatic spread.

A class of biological substances called the proteoglycans form the ground substance in the extracellular matrix of connective tissues. These proteoglycans are polyanionic substances of high molecular weight and contain many different types of heteropolysaccharide side chains covalently linked to a polypeptide backbone. These proteoglycans may contain over 95% carbohydrates. The polysaccharide groups of the proteoglycans were formerly called mucopolysaccharides but now are preferably termed glycosaminoglycans since all contain derivatives of glucosamine or galactosamine.

A variety of enzymes may be involved in the normal metabolic degradation of proteoglycans. Initial proteoglycan degradation often involves proteolysis to separate or digest protein components. Such proteolysis results in the production of glycosaminoglycans. The glycosaminoglycans in turn are subject to glycosaminoglycan endoglycosidase enzymic action which produces smaller glycosaminoglycan fragments. The glycosaminoglycans or fragments thereof are subject to glycosaminoglycan exoglycosidase enzymic action which produces monosaccharides from the non-reducing ends of glycosaminoglycans.

An increasing interest in the endoglycosidases has arisen in recent years because of a possible relationship of these enzymes with tumor invasiveness and tumor metastatic activity. Nicolson (1982, Biochem. Biophys. Acta. V 695, pp 113-176) reviewed a variety of oligosaccharide-degrading enzymes (pp 141-142) reported to be of interest in malignant disease. Nicolson (1982, J. Histochem. & Cytochem. V 30, pp 214-220) described a proposed mechanism for tumor cell invasion of endothelial cell basal lamina and a related production of degradation products from proteins and glycosaminoglycans. Kramer et al., (1982, J. Biol. Chem. V 257, pp 2678-2686) reported a tumor-derived glycosidase capable of cleaving specifically glycosaminoglycans and releasing heparan sulfate-rich fragments.

Irimura et al., (1983a, Analyt. Biochem. V 130, pp 461-468) describe high-speed gel-permeation chromatography of glycosaminoglycans. Heparan sulfate degrading activity of melanoma cells was measured by using this chromatographic procedure. Nakajima et al., (1983, Science, V 220, pp 611-613) described a relationship of metastatic activity and heparan sulfate degrading activity in melanoma cell lines. The disappearance of higher molecular weight heparan sulfate was followed by polyacrylamide gel electrophoresis, staining and densitometry.

Vlodavsky et al., (1983, Cancer Res. V 43, pp 2704-2711) described the degradation by two T-lymphoma cell lines of $^{35}S$ labeled proteoglycans from confluent endothelial cells. The highly metastatic line had much higher $^{35}S$ liberating activity than did the low metastatic line.

Irimura et al., (1983c, Proc. Am. Soc. Cancer Res. V 24, p 37, abstract 144), using high performance liquid chromatography, describe heparan sulfate degradative enzyme activity of melanoma cells. Nakajima et al., (1984, J. Biol. Chem. V 259, pp 2283-2290) describe characterizations of metastatic melanoma heparanase. High speed gel permeation chromatography and chemical analyses were used in a description of functional substrates and products formed. Nakajima et al. (1986, Anal. Biochem., in press) synthesized a solid-phase substrate for heparanase by crosslinking radiolabeled and reductively aminated HS to amino-reactive agarose beads via one covalent linkage. This solid-phase substrate was used for the measurement of heparanase activity in various human melanoma cell lines (Nakajima et al., (1986) Cancer Letters, V 31, pp 277-283) and sera from mammary adenocarcinoma-bearing rats and malignant melanoma patients (Nakajima et al., (1986) In: Cancer Metastasis: Experimental and Clinical Strategies, D. R. Welch, B. K. Bhuyan, L. A. Liotta, eds. Alan R. Liss, Inc., New York, pp 113-122).

From the foregoing it may be seen that significant interest exists in convenient, accurate and reproducible endoglycosidase assays and production of potent heparanase inhibitors, particularly since endoglycosidases may play critical roles in the establishment of tumor metastases.

The ability of tumor cells to invade host tissues and metastasize to distant, often specific organ sites, is one of their most important properties. Metastasis formation occurs via a complex series of unique interactions between tumor cells and normal host tissues and cells. These processes involve several discrete and selective steps such as: invasion of surrounding tissues, penetration of lymphatics of blood vessels and transport in lymph or blood, or dissemination into a serous cavity, arrest and invasion at distant sites, and survival and growth to form secondary lesions.

Basement membranes are continuous sheets of extracellular matrix composed of collagenous and non-collagenous proteins and proteoglycans that separate parenchymal cells from underlying interstitial connective tissue. They have characteristic permeabilities and play a role in maintaining tissue architecture. Metastasizing tumor cells must penetrate epithelial and endothelial basement membranes during invasion and metastasis, and the penetration and destruction of basement membranes by invasive tumor cells has been observed using electron microscopy. Since basement membranes are rigid structures formed from unique sets of macromolecules, including type IV collagen, laminin, heparan sulfate (HS), proteoglycan and fibronectin, the successful penetration of a basement membrane barrier probably requires the active participation of more than one tumor cell-associated enzyme.

Due to its unique physical and chemical properties such as its polyanionic character and barrier properties against macromolecules (Kanwar et al., 1980 J. Cell. Biol. V 86, pp 688-693), HS is an important structural component of basement membranes. HS binds to fibronectin, laminin and type IV collagen, and these molecules have been collectively observed in the basal lamina using antibodies raised against each component. HS may be involved in basal lamina matrix assembly by promoting the interactions of collagenous and non-collagenous protein components while protecting them against proteolytic attack. Thus, the destruction of HS proteoglycan barrier could be important in basement membrane invasion by tumor cells.

The interactions between malignant cells and vascular endothelium have been studied using monolayers of cultured vascular endothelial cells that synthesize an extracellular matrix resembling a basement membrane. With this model, it has been found that metastatic B16 melanoma cells degrade matrix glycoproteins, such as fibronectin, and matrix sulfated glycosaminoglycans, such as heparan sulfate. Since HS was released in solution as fragments approximately one-third their original size, it has been proposed that metastatic tumor cells characteristically have a HS endoglycosidase.

The relation between metastatic properties and the ability of five B16 melanoma sublines of various implantation and invasion characteristics to enzymatically degrade subendothelial extracellular matrix indicated that highly invasive and metastatic B16 sublines degraded sulfated glycosaminoglycans faster than did sublines of lower metastatic potential (Nakajima et al., (1983), Science V 220, p 611), and intact B16 cells (or their cell-free homogenates) with a high potential for lung colonization also degraded purified heparan sulfate at higher rates than did B16 cells with a poor potential for lung colonization (ibid).

The abilities of B16 cells to degrade HS from various origins and other purified glycosaminoglycans (heparin, chondroitin 4-sulfate, chondroitin 6-sulfate, dermatan sulfate, keratan sulfate, and hyaluronic acid) have been studied. In order to analyze glycosaminoglycan degradation products, an analytic procedure was developed using high-speed gel permeation chromatography (Irimura et al., (1983a) Anal. Biochem. V 130, p 161; Nakajima et al., (1984) J. Biol. Chem. V 259, p 2283). HS metabolically labeled with $^{35}$S-sulfate was purified from basement membrane producing EHS sarcoma and PYS-2 carcinoma cells, and subendothelial matrices of bovine aortic endothelial (BAE) and corneal endothelial (BCE) cells (ibid). HS molecules purified from bovine lung and other glycosaminoglycans were labeled with tritium at their reducing termini using $^3$H-NaBH$_4$. These labeled glycosaminoglycans were incubated with B16 cell extracts in the absence or presence of D-saccharic acid 1,4-lactone, a potent exobeta-glucuronidase inhibitor, and degradation fragments were analyzed by high-speed gel permeation chromatography.

HS isolated from the various origins described above were all degraded into fragments of characteristic molecular weight, in contrast to hyaluronic acid, chondroitin 6-sulfate, chondroitin 4-sulfate, dermatan sulfate, keratan sulfate, and heparin, which were essentially undegraded. Heparin, but not other glycosaminoglycans, inhibited HS degradation. The time dependence of HS degradation into particular molecular weight fragments indicated that melanoma heparanase cleaves HS at specific intrachain sites (ibid). In order to determine specific HS cleavage points, the newly formed reducing termini of HS fragments were investigated by: labeling with $^3$H-NaBH$_4$; hydrolysis to monosaccharides; and analysis of these saccharides by paper chromatography. Since $^3$H-reduced terminal monosaccharides from HS fragments were overwhelmingly (>90%) L-gulonic acid, the HS-degrading enzyme responsible was an endoglucuronidase (heparanase).

HS-degrading endoglucuronidases have been found in various tissues, such as human skin fibroblasts, rat liver cells, human placenta, and human platelets. HS-degrading endoglucuronidases in mammalian cells were reported previously by other investigators to be "heparitinases" to indicate heparitin sulfate (heparan sulfate)-specific endoglycosidase. However, heparitinase originally was used to designate an elimination enzyme (EC 4.2.2.8) in Flavobacterium heparinum, and this enzyme cleaves non-sulfate and monosulfated 2-acetoamido-2-deoxy-alpha-D-glucosyl-D-hexuronic acid linkages of HS. Since HS-specific endoglycosidases in mammalian cells are endoglucuronidases, except for one found in skin fibroblasts, it was proposed that mammalian cell endoglucuronidases capable of degrading HS should be called "heparanases", consistent with the currently used term "heparan sulfate".

High heparanase activity in human melanoma cells was demonstrated using a solid-phase substrate, partially N-desulfated N-[$^{14}$C] acetylated HS crosslinked to agarose beads via one covalent linkage (Nakajima et al., (1986) Cancer Letters, V 31, pp 277–283; Nakajima et al., (1986) Anal. Biochem. in press). All of the 15 human melanoma cell lines tested were found to have heparanase activity and almost all possessed high activities comparable or greater than that of the murine B16-F1 melanoma line. Human A375 melanoma variants of high lung metastatic potential in athymic nude mice had significantly higher heparanase activities than did A375 parental cells of low metastatic potential.

High heparanase activity was also found in the sera from highly metastatic tumor-bearing animals and malignant melanoma patients (Nakajima et al, (1986) In: Cancer Metastasis: Experimental and Clinical Stategies, D. R. Welch, B. K. Bhuyan, L. A. Liotta, eds., Alan R. Liss, Inc., New York, pp 113–122). A significant difference in serum heparanase activity was found between a group of normal adults and a group of malignant melanoma patients (N=35, p<0.05). The mean values of serum heparanase activities in normal adults and malignant melanoma patients were 3.97 and 9.43 mg HS/h/ml serum, respectively. Some of the patients having documented lymph node metastases had 4 to 6-fold higher serum heparanase activities than normal adults.

Anticoagulants, such as heparin, warfarin, dextran sulfate and Ancrod; (Agkistrodon rhodostoma venom protease, Abbott) have been used to prevent blood coagulation and reduce the formation of metastatic tumor cell thrombi in the blood which lodge more effectively in the microcirculation Hilgard et al., Eur. J. Cancer, V 12, pp 755–762, 1976). H. Ludwig (Gynakologe, V 7, pp 1–10, 1974) reported longer recurrence-free intervals and less metastases in patients during irradiation of their gynaecological cancers. Heparin has been used as an adjuvant therapy agent with combination chemotherapy of inoperable lung cancer with enhanced therapeutic effects (Elias, Proc. Amer. Assoc. Cancer Res., V 14, p 26, 1973, Abst.). L. Michaels (Lancet, V 2, pp 832–83, 1964) found that the cancer incidence and death rate was lower than expected for patients receiving heparin. Dextran sulfate (M$_r$—7,000) has been used to inhibit metastasis of rat lung tumors, and human lung cancer patients have received long term oral dextran sulfate. Although the antimetastatic effects of dextran sulfate were marginal in cancer patients, this was probably due to the low intestinal absorption of dextran sulfate (Suemasu, Gann Monogr., V 20. pp 163–172, 1977).

Heparin and related sulfated glycoconjugates with anticoagulation properties, such as dextran sulfate have been used experimentally as antimetastatic agents (Tsubura et al., (1977) Gann Monogr. Cancer Res., V 20, pp 147-153; Hilgard, (1984) in Cancer Invasion and Metastasis, Biologic and Therapeutic Aspects, Nicolson et al., eds, pp 353-360 Raven Press, N.Y.) The basis for this use was the assumption that platelet aggregation, together with activation of the coagulation cascade, enhanced the formation of tumor embolism and increased implantation and metastatic colonization of blood-borne tumor cells. In other studies on the effects of heparin on metastasis, however, heparin administration increased, decreased, or had no effect on tumor cell dissemination and organ colonization, depending on the experimental system. Mechanisms other than the anticoagulation effects of heparin on tumor metastasis were suggested by these results, but the possible involvement of tumor heparanase had not been considered. The present invention relates to heparin derivatives without anticoagulant properties and which inhibit the heparanase activity of metastatic mouse melanoma cells. These substances were useful as tools for in vitro and in vivo studies involving the role of heparanase in tumor invasion and metastasis.

Using oral administration of heparin in combination with hydrocortisone, it was reported that complete regression of established transplantable tumors in mice could occur through inhibition of tumor angiogenesis (Folkman et al., Science, V 221, pp 719-725, 1983). This suggested that anti-angiogenic substances could be used for cancer therapy (J. Folkman in: Important Advances in Oncology, de Vita et al., eds, pp 42-62, J. B. Lippincott, Philadelphia, 1985). In such studies heparin was administered in the drinking water of animals. For example, hamsters have been inoculated with transplantable pancreatic carcinoma cells and have been treated by receiving heparin or hexuronyl hexaminoglycan sulfate, a heparin derivative, in their drinking water at concentrations of 10 mg/ml with hydrocortisone (0.5 mg/ml). After treatment for 6-9 days, the tumors were examined. In 3 out of 4 of the tumors the hexuronyl hexaminoglycan sulfate plus hydrocortisone resulted in significant reductions in growth rate in vivo and significant inhibitions of capillary endothelial cell migration in Boyden chambers in vitro (Rong et al., Cancer, V 57, pp 586-590, 1986).

Proliferation of vascular smooth muscle cells has been shown to be an important step in the pathogenesis of arteriosclerosis (Ross et al., Science, V 180, pp 1332-1339, 1973). Commercial heparin preparations have been separated into anticoagulant and non-anticoagulant mixtures by use of antithrombin to remove the anticoagulant heparin. Both of these forms of heparin significantly inhibit the growth of smooth muscle cells in vitro (Hoover et al., Circulation Res., V 47, pp 578-583, 1983). Using the heparin preparations at a concentration of 10 ug/ml resulted in approximately 50% inhibition of $^3$H-thymidine uptake by arterial smooth muscle cells, which is indicative of growth inhibition. Administration of anticoagulating and non-anticoagulating heparin fractions inhibited intimal smooth muscle proliferation, as determined by the total plaque volume two weeks after arterial injury. Non-anticoagulating heparin given at a dose of 100 USP units per kg body weight per hour in Sprague-Dawley rats resulted in 77% inhibition of myointimal growth (Guyton et al., Circulation Res., V 46, pp 625-634, 1980).

Further studies indicated that the minimum fragment size of heparin, which was growth inhibitory toward vascular smooth muscle cells, was a hexasaccharide, and the maximum anti-proliferative activity was obtained with a 12-residue heparin. Most modified heparins (totally desulfated, N-desulfated, and totally desulfated re-N-acetylated) lost their anti-proliferative activity, but the N-desulfated N-resulfated heparin and the N-desulfated N-acetylated heparin retained full growth inhibitory properties (Castellot et al., J. Cell. Physiol., V 120, pp 315-320, 1984). Diseases, such as arteriosclerosis, develop over a long period of time. Therefore, the main use of such treatments might be in vascular damage due to trauma or surgery, such as artery vein grafts or arteriovenous shunts for kidney dialysis.

SUMMARY OF THE INVENTION

The present invention comprises novel compositions and a method for impeding the formation of tumor metastasis or tumor invasiveness in a host. The spread of melanomas and mammary carcinomas is inhibited by the derivatives described herein. The method comprises parenteral administration to the host of a glycosaminoglycan derivative substantially devoid of anticoagulation activity and which is an effective inhibitor of heparanase activity. Suitable glycosaminoglycan derivatives, which are useful as novel compositions in the method of the invention, include glycosaminoglycan derivatives of the following structure:

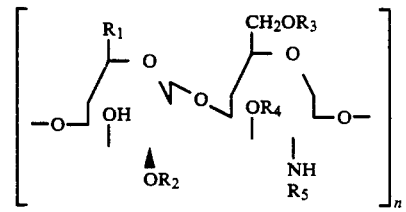

Where
$R_1$ is —COOH or —CH$_2$OH and the configuration of the carbon atom to which $R_1$ is bound is D or L;
$R_2$ is —H or —SO$_3^-$;
$R_3$ is —H or —SO$_3^-$;
$R_4$ is —H or —SO$_3^-$;
$R_5$ is —H, —SO$_3^-$ or —CO—CH$_3$;
n is 3 to 30; and
each of the terminal monomeric units is a monomeric repeating unit with the terminal oxygen atom being bound to a blocking group.

The blocking group may be a small alkyl or acyl group having less than about 5 carbon atoms and preferably is —H, —CH$_3$, —SO$_3$ or CO—CH$_3$.

The glycosaminoglycan derivates of the present invention may be prepared by derivatization of heparin obtained from natural sources or they may be prepared by a variety of conventional synthetic techniques. Administration to a tumor-bearing host of an effective amount of a glycosaminoglycan derivative of the invention results in the exposure of host-borne tumor cells thereto. Such exposure to effective levels of the derivative results in the inhibition of tumor heparanase activity and a lessening of tumor invasiveness and metastatic spread.

Heparin, a glycosaminoglycan which is effective both as a heparanase inhibitor and an anti-clotting agent, is a preferred glycosaminoglycan for derivatization. Upon derivatization according to the present invention, heparin may be converted into a glycosaminglycan derivative substantially devoid of anticoagulant activity but yet being an effective inhibitor of heparanase activity. Reduction of heparin carboxyl groups results in the production of a glycosaminoglycan derivative inhibitory to heparanase activity but without substantially anticoagulant activity. Heparanase-inhibiting glycosaminoglycan derivatives having no substantial anti-coagulant activity may also be prepared from heparin, for example, by: at least partial N-desulfation and then N-acetylation; or at least partial N-, O-desulfation followed by N-resulfation.

BRIEF DESCRIPTION OF THE DRAWINGS

FIG. 8: Adhesion of B16 melanoma cells to bovine aortic endothelial cell monolayers.

BRIEF DESCRIPTION OF PREFERRED EMBODIMENTS

Figure 1:
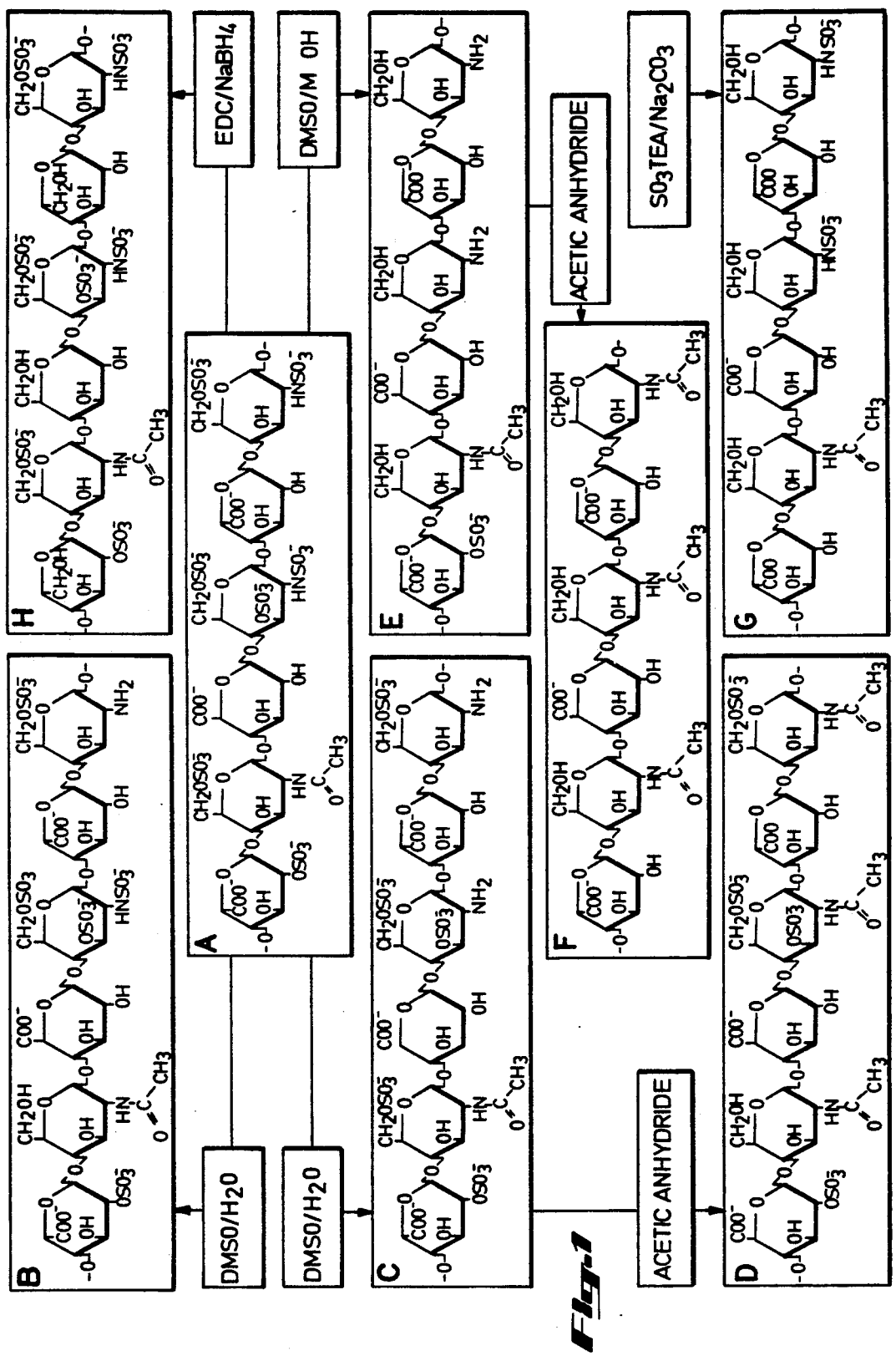
FIG. 1: Monomeric structural formulas which represent derivatives of heparin used in this study (actual structures obtained by derivatization are averages of monomerics units shown). a, Intact heparin; b, Partially N-desulfated heparin; c, completely N-desulfated heparin; d, N-acetylated N-desulfated heparin; e, N- and O-desulfated heparin; f, N-acetylated N- and O-desulfated heparin; g, N-resulfated N- and O-desulfated heparin; h, carboxy-reduced heparin.

Heparanase from metastatic melanoma cells is an endobeta-glucuronidase which is specific for HS (Irimura et al., (1983b), Gann Monogr. Cancer Res., V 29, pp 35–46; Nakajima et al., (1984) J. Biol. Chem, V 259, pp 2283–2290). Although heparin is structurally and biosynthetically related to HS, it is a poor substrate for heparanase, and it interferes with HS degradation (Nakajima et al., (1984)). Structural differences between heparin and HS are based primarily on the degrees of sulfation of glucosamine residues, and the relative contents of iduronic acid. The heparanase-inhibitory activity of heparin should be determined, therefore, by its sulfate as well as its carboxy groups. If one of these group were responsible for heparanase inhibition, this information should be useful in developing specific heparanase inhibitors. Furthermore, since sulfamine and O-sulfate groups of glucosamine, O-sulfate groups of iduronic acid, and carboxy groups of uronic acid are essential for heparin's anticoagulation activities, some of the chemical modifications should produce heparin derivatives that inhibit heparanase activity but are not anticoagulants.

The glycosaminoglycan derivatives of the invention are derivatives of heparin or heparin analogs which are effective inhibitors of heparanase while being substantially devoid of the anticoagulant activity that is characteristic of heparin. In particular, preferred compounds of the invention are glycosaminoglycan derivatives of the following structure:

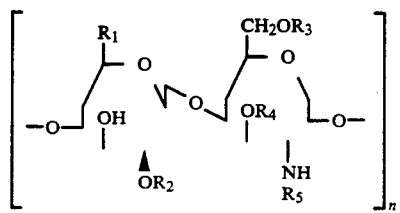

Where
$R_1$ is —COOH or —CH$_2$OH and the configuration of the carbon atom to which $R_1$ is bound is D or L;
$R_2$ is —H or —SO$_3^-$;
$R_3$ is —H or —SO$_3^-$;
$R_4$ is —H or —SO$_3^-$;
$R_5$ is —SO$_3^-$ or —CO—CH$_3$; and
n=3–30;
provided that: when $R_1$ is —CH$_2$OH, at least 50% of $R_2$, $R_3$ and $R_5$ is —SO$_3^-$;
when $R_1$ is —COOH, and $R_2$, $R_3$ and $R_4$ are —H, $R_5$ is —SO$_3^-$;
when $R_1$ is —COOH, and at least 50% of $R_2$, $R_3$ and $R_4$ is —SO$_3^-$, $R_5$ is —CO—CH$_3$; and
each of the terminal monomeric units is a repeating monomeric unit having a terminal oxygen atom bound to a blocking group.

The preferred glycosaminoglycan derivatives of the invention include those having a monomeric repeating structure as given above and may be utilized as salts. Pharmaceutically acceptable salts, for example, potassium or magnesium salts, of the glycosaminoglycan derivatives described above are also suitable for use in the method of the invention and are within the scope of the present invention.

The glycosaminoglycan derivatives of the invention, which are oligomeric and/or polymeric forms of the monomeric repeating structure given above, suitably have a molecular weight between about 1,000 and about 15,000. These glycosaminoglycan derivatives have a preferred molecular weight between about 10,000 and about 12,500.

The present invention involves a new method for inhibiting the spread of cancer. This method relates to the inhibition of glycosaminoglycan-degrading enzymes which may play significant roles in the invasive or metastatic behavior of tumors. Described herein are newly devised inhibitors for heparanase, an enzyme often found in tumors, which degrades glycosaminoglycans of the extra-cellular matrix or basement membrane such as heparan sulfate. Such degradation is involved with tumor penetration of and attachment to biological structures.

Heparin is a preferred precursor for the synthesis of these cancer-inhibiting substances. Other glycosaminoglycans may be used as these substances or precursors to such substances. These other glycosaminoglycans may include, for example, hyaluronic acid, chondroitin 4-sulfate, chondroitin 6-sulfate, dermatan sulfate, keratan sulfate or heparan sulfate. Functionally, these cancer-inhibiting substances have qualities of impeding the activity of glycosaminoglycan-degrading enzymes and being substantially devoid of anticoagulant activity. A generally desireable chemical property of usable cancer-inhibiting glycosaminoglycan substances is the presence of sulfated amino groups.

In a general sense the cancer-inhibiting substances of the present invention may be synthesized by, for example:

(1) First, identifying a material, usually a sulfated glycosaminoglycan, which inhibits heparanase and has anticoagulation activity. Then, chemically altering this material to substantially remove anticoagulation activity while enhancing or at least not removing heparanase-inhibitory activity. Many of the Examples appended hereto illustrate this approach; or, (2) First, obtaining a glycosaminoglycan which substantially neither has anticoagulant activity nor inhibits heparanase. Then, chemically altering the glycosaminoglycan, for example by sulfation of amino groups, to produce a glycosaminoglycan derivative having heparanase inhibitory activity but being substantially devoid of anticoagulant activity.

Chemically modified substances may be assayed by methods described herein to follow effects upon anticoagulant activity and heparanase-inhibitory activity. When derivatives having these properties are non-toxic at levels adequate to inhibit heparanase activity are obtained, they would be suitable for the practice of the methods of the present invention.

In chemotherapeutic usage, the cancer-inhibiting substances of the present invention will be administered parenterally at dosages between about 30 mg/day and about 250 mg/day, preferably between about 30 mg/day and about 100 mg/day. However, some variation in dosage will necessarily occur depending on the condition of the subject being treated and the potency of the particular substance. The person responsible for administration will, in any event, determine the appropriate dose for the individual subject.

In breast cancer, adjuvant chemotherapy, with or without hormone treatment, has been used for treatment of operable breast cancer (Fisher et al., NCI Monograph, V 1, pp 35-43, 1986) At M.D. Anderson Hospital, adjuvant chemotherapy trials have utilized, as a minimum treatment protocol, a program consisting of 5-fluorouracil, doxorubicin, and cyclophosphamid (Buzdar et al., NCI Monograph, V 1, pp 81-85, 1986). In more recent studies cycles of chemotherapy were repeated at 28 day intervals using continuous infusion pumps to administer the chemotherapeutic agents. In breast cancer, administration of non-anticoagulation heparin derivatives may be used at two times during therapy: (1) during surgery of the primary tumor and post-operatively to inhibit the dissemination of cancer cells caused by surgical manipulation, and (2) during the continuous infusion of chemotherapeutic drugs, to prevent tumor cell dissemination in the blood and capillary lodgement caused by drug damage of normal tissues, such as endothelial cells (Nicolson et al., Cancer Res., V 45, pp 331–336, 1985). The heparin derivatives would be administered intravenously in amounts between about 30 mg/day and about 250 mg/day, preferably between 30 mg/day and about 100 mg/day. However, some variation in dosage will necessarily occur depending upon the condition of the subject being treated and the potency of the particular substance. The physician responsible for administration will determine the appropriate dose for the individual subject.

In malignant melanoma the following example of adjuvant therapy has been used to treat metastatic disease. Patients have been treated with an adjuvant sequence of cisplatin, vinblastine and bleomycin intravenously every three weeks for a total of three cycles (Johnson et al., Cancer Treatment Rep., V 69, pp 821–824, 1985). The heparin derivatives would be administered intravenously, as described above, during administration of the chemotherapeutic agents.

The novel compounds of the invention may be administered alone or in combination with pharmaceutically acceptable carriers and will typically be formulated in a unit injectable dosage form (solution, suspension, emulsion), preferably in a pharmaceutically acceptable carrier which is inherently non-toxic and non-antigenic. In this regard, suitable carriers for formulations in accordance with the invention include saline, Ringer's solution, mannitol, dextrose solution, and normal serum albumin. Non-aqueous carriers such as fixed oils and ethyl oleate may also be used. The carrier may also contain small amounts of additives such as substances which enhance isotonicity and chemical stability, for example, buffers and preservatives. In any case, the formulations in accordance with the invention shall contain an effective amount of glycosaminoglycan derivative to impede the spread of cancer cells by metastases or invasion.

These aqueous solutions are especially suitable for parenteral administration. In this connection, the sterile aqueous media employed are all readily available by standard techniques known to those skilled in the art. Treatment in accordance with the invention is performed in a manner such that a maximal inhibition of tumor spread will occur. This will involve the intraperitoneal, intravenous, intraarterial or intramuscular injection of the maximum tolerated dose of glycosaminoglycan derivative which is effective in invoking the desired inhibition of cancer cell spread in the patient.

The following examples are presented to describe preferred embodiments and utilities of the present invention and are not meant to limit the present invention unless otherwise stated in the claims appended hereto.

EXAMPLE 1

Materials and Methods

Chemical Modification of Heparin. Chemical modifications and the resultant compounds used in this study are schematically shown in FIG. 1. Heparin from porcine intestinal mucosa (sodium salt) was purchased from Sigma Chemical Co. (St. Louis, Mo.). One gram of heparin was dissolved in 30 ml of water and applied to a 1.5×8 cm column of Dowex 50W×8, 50–100 mesh (H+ form) (BioRad, Richmond, Calif.) at 4° C. The pass-through fraction eluted with water was neutralized immediately with pyridine and the pH adjusted to between 6 and 7 (Nagasawa, et al., (1980a) Meth. Carbohyd. Chem., V 8, pp 287–289). After dialysis against water, the heparin pyridinum salt was collected by lyophilization. Partial N-desulfation, complete N-desulfation, and complete N- and O-desulfation, starting with 100 mg each of heparin pyridinium salts, were achieved by solvolysis in 10 ml of dimethylsulfoxide (ACS grade, Fisher Scientific, Fair Lawn, N.J.) containing water or methanol as described by Nagasawa, et al. ibid and Nagasawa, et al. (1980b) Meth. Carbohyd. Chem., V 8, pp 291–294. Reaction conditions were 10% water in dimethyl sulfoxide at 20° C. for 1 h for partial N-desulfation, 10% water in dimethyl sulfoxide at 80° C. for 5 hr for complete N-desulfation, and 10% anhydrous methanol in dimethylsulfoxide at 80° C. for 18 h for complete N- and O-desulfation. After these reactions, the mixtures were cooled and 1M sodium hydroxide was added to adjust the pH to between 8.5 and 9.5; the mixtures were dialyzed against running tap water and then against distilled water.

N-acetylation of N-desulfated and N- and O-desulfated heparin was performed with acetic anhydride under alkaline conditions as follows: fifty milligrams of modified heparin were dissolved in 5 ml of 4.5M sodium acetate plus 1.0 ml of methanol and added to five portions of 1.0 ml of acetic anhydride at 10 min intervals. After 1 hr incubation with occasional mixing, the reaction mixture was dialyzed against running tap water, then distilled water, and was finally lyophilized.

The N-resulfation reaction was performed by sulfation with a triethylamine sulfur trioxide complex prepared according to Cherniak and Davidson's (1964) method (J. Biol. Chem., V 239, pp 2986–2990). Complete N- and O-desulfated heparin (50 mg) was dissolved in 2 ml of 1.0M sodium carbonate and added to 50 mg of triethylamine sulfur trioxide. The atmosphere was replaced with nitrogen, and the mixture was heated at 50° C. for 24 h with occasional agitation. The resulfated heparin was dialyzed against running tap water, then distilled water, and finally lyophilized. Carboxyl-reduced heparin was prepared from sodium salt of porcine intestinal mucosa heparin as described by Taylor et al. (1976) (Meth. Carbohyd Chem., V 7, pp 149–171) by use of sodium borohydride (Aldrich Chemical Co., Milwaukee, Wis.) and N-ethyl-N'-(3-dimethylaminopropyl)-carbodiimide-hydrochloride (Fluka Chemical Co., Hauppauge, N.Y.).

Analytical Procedures. The homogeneity of the chemically modified heparins was assessed by cellulose acetate electrophoresis and high-speed gel-permeation chromatography. Electrophoresis was performed on a 7.6×7.6 cm Titan III Zip Zone cellulose acetate sheet (Helena Laboratories, Beaumont, Tex.) in 0.5M/0.5M pyridineacetate buffer, pH 5.0 (Hata et al., (1979), Anal. Biochem., V 45, pp 412–469). Each 1 μl sample was applied to 2.0 cm wide stacking zone which was blotted with water before the sample application (Cappeletti et al., (1979) Anal. Biochem., V 99, pp 311–320). Electrophores was carried out under constant voltage (75V) for 45 min. During the run the sheet was immersed in petroleum ether cooled under ice. The cellulose acetate sheet was then stained with 0.1% toluidine blue O in 1% acetic acid and destained with 1% acetic acid.

High-speed gel permeation chromatography was performed as described previously (Irimura et al., (1983a) Anal. Biochem., V 130, pp 461–468) using a Constametric III (LDC-Milton Roy, Riviera Beach, Fla.) with a single 0.7×75 cm stainless steel column packed with Fractogel TSK HW-55(S). Elution was accomplished with 0.2M sodium chloride at flow rates of 1.0 ml/min or 0.75 ml/min. Absorption at 210 nm was monitored for the analogs of chemically modified heparin. For the qualitative examination of radiolabeled HS-degradation products, each fraction corresponding to 30-sec elution was collected into plastic scintillation vials, and radioactivity in each vial was determined after the fraction was mixed with 3.0 ml of Hydrofluor (National Diagnostics, Somerville, N.J.).

Source of Heparanase. Highly invasive mouse B16 melanoma (B16-BL6) cells were provided by Dr. I. J. Fidler, (M.D. Anderson Hospital, Houston, Tex.) and were cultured as previously described (Irimura et al., (1983a) and Irimura et al. (1984)). Cell extracts were prepared in 5 mM Tris-HCl buffer, pH 7.4, containing 0.25M sucrose, 50 $\mu$M calcium chloride, 10 $\mu$M phenylmethylsulfonylfluoride, and 0.2% Nonidet P-40 (Irimura et al., (1983). The melanoma extracts were stored frozen at $-80°$ C. and used as crude heparanase.

Radio-Labeling of HS. $^{14}$C- or $^3$H-heparan sulfate was prepared by chemical deacetylation and radioactive reacetylation. Nine milligrams of bovine lung HS were dried with 0.1 mg of hydrazine sulfate over phosphorous pentoxide under vacuum at 50° C. for 48 h. Anhydrous hydrazine (0.5 mg, Pierce Chemical, Rockford, Ill.) was added to the dried HS and the mixture heated in a tightly screwed tube under nitrogen atmosphere at 100° C. for 1 h. After the reaction, the hydrazine was removed by repeated evaporation with toluene over sulfuric acid desiccant under vacuum conditions. To separate deacetylated HS from residual reagents and partial degradation products, the completely dried residue was dissolved in 0.5 ml of water and subjected to gel filtration on a 0.8$\times$30 cm column of BioGel P-10 and elution with distilled water. The void volume fraction was collected and lyophilized, and the yield by weight was about 60%. N-deacetylated HS was then N-acetylated with 50 uCi of $^{14}$C-acetic anhydride (10 mCi/mmole: New England Nuclear, Boston, Mass.) or 5 mCi $^3$H-acetic anhydride (400 mCi/mmole:NEN) in 0.5 ml of 4M sodium acetate for 18 hrs. N-acetylation was completed by addition of 0.1 ml of unlabeled acetic anhydride to the reaction mixture and incubation for 1 h. $^{14}$C- or $^3$H-HS was purified on a BioGel P-10 column as described above.

High-Performance Liquid Chromatography [HPLC] Assay for Heparanase. Fifty microliters of melanoma extract (equivalent to $10^6$ cells) were mixed with chemically modified heparin (5 mg/ml in water), 50 $\mu$l of 4$\times$heparanase assay buffer (0.4 sodium phosphate buffer, pH 5.8, containing 0.4% Triton X-100, 0.6M sodium chloride, and 0.4% sodium azide) and about 3000 cpm of $^{14}$C-HS. Incubation was performed at 37° C. with continuous gentle mixing for 6 h. The reaction mixture was placed on ice, 20 $\mu$l of 50% trichloroacetic acid was added, and incubation continued on ice for 10 min. After centrifugation at 9000$\times$G for 5 min in a Microfuge B (Beckman Instruments, Irvine, Calif.), the supernatant was injected into the gel-permeation chromatography system and analyzed as described above (Irimura et al., (1983a)).

Preparation of Solid-phase Substrates for Heparanase and Inhibitor Assays. For the solid-phase heparanase assay, $^3$H-HS was aminated at the reducing terminal with 2M ammonium acetate in the presence of 0.4M sodium cyanoborohydride in 50% methanol, at 50° C. for 6 days. Aminated $^3$H-HS was purified by gel filtration as described above, and the resulting solution was diluted to 0.1M in sodium carbonate. To $10^6$ cpm of aminated $^3$H-HS, 1.0 ml of Affi-Gel 15 (Bio Rad) gel beads was added after they were washed with isopropanol and chilled water. The coupling reaction was continued at 4° C. for 48 h with continuous agitation. The gel beads were then reacted with 0.1M glycine monomethyl ester dissolved in 0.1M sodium carbonate for 1 h at room temperature and then washed with 4M sodium chloride repeatedly to remove noncovalently attached $^3$H-HS from the beads.

Solid-phase Assays for Heparanase and Heparanase Inhibitors. $^3$H-HS-agarose was suspended in Dulbecco's phosphate buffered saline (DPBS) at about 20% (v/v). The incubation conditions for the solid-phase assay were identical to those of the HPLC assay, except that 75 $\mu$l of the $^3$H-HS-agarose suspension was used instead of the HS so that the incubation mixture consisted of B16 melanoma extract, chemically modified heparins, 4$\times$heparanase assay buffer, and $^3$H-HS-agarose suspension. After incubation, the reaction mixture was placed on ice, chilled 5% trichloroacetic acid (50 ul) added, the mixture incubated for 10 min, and centrifuged. Radioactivity in the supernatant and the pellet was determined separately after mixing with Hydrofluor.

Experimental Metastatic Lung Colonization of Melanoma Cells. Male C57BL/6 mice 4 to 6 weeks old were obtained from Charles River, Inc. (Kingston, Md.) and quarantined for 2 weeks. Animals were fed normal rodent chow and unchlorinated spring water. B16-BL6 cells were grown to subconfluence, detached from plastic dishes by incubating in 2 mM EDTA, 0.14M NaCl and 10 mM sodium phosphatebuffer, pH 7.4, for 5–10 min, and suspended in a 1:1 mixture of Dulbecco's modified minimum essential medium and Ham's F12 medium. The cells were incubated with heparin, N-acetylated N-desulfated heparin, N-resulfated N and O-desulfated heparin or carboxy-reduced heparin (each 0.5 mg/ml in the media described above) at 4° C. for 2 hrs. Treated or untreated cells (5$\times$10$^4$/0.1 ml) were injected intravenously to each mouse. Mice were killed 20 days later and autopsied. The numbers of pulmonary tumor nodules were counted after the lung was perfused via the trachea with 4% formalin in Dulbecco's phosphate buffered saline. Extrapulmonary tumor formation was assessed in each animal and recorded.

EXAMPLE 2

Chemically Modified Heparins

Figure 2:
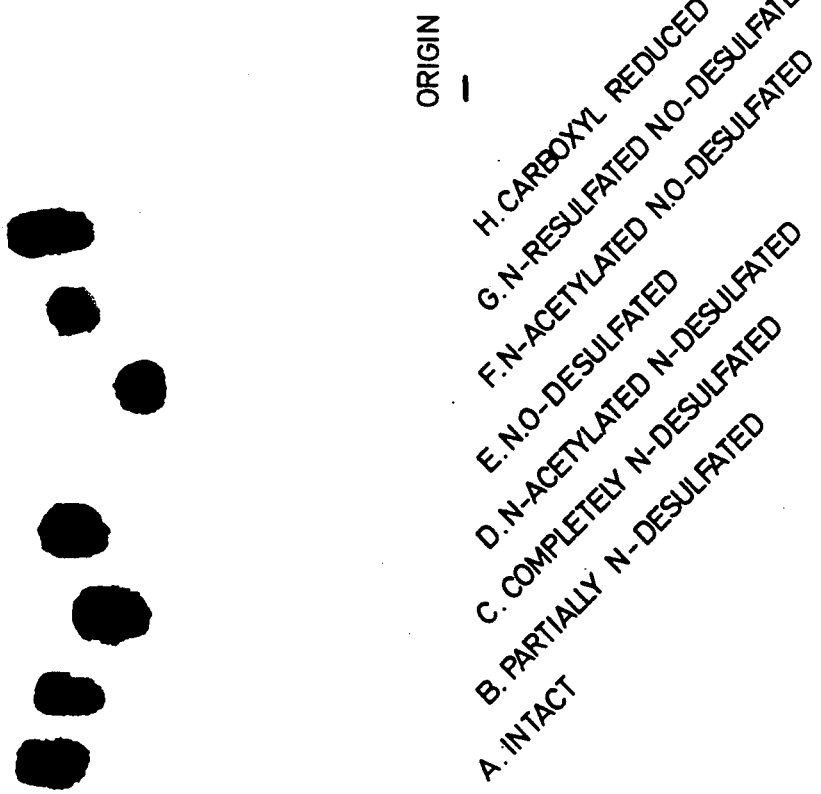
FIG. 2: Cellulose acetate sheet electrophoresis of chemically modified heparins. The sheet is 7.6 cm in total length, with 1.5 cm of stacking area blotted with water and 5.0 cm of separating area blotted with a 0.5M pyridine/0.5M acetic acid, pH 5.0 buffer. The electrodes are in the same buffer. Electrophoresis is performed under constant voltage (12 V/cm) at 4° C. for 45 min. After electrophoresis, the sheet was stained with toluidine blue (0.1% toluidine blue in 1% acetic acid) and destained with 1% acetic acid.
Figure 3:
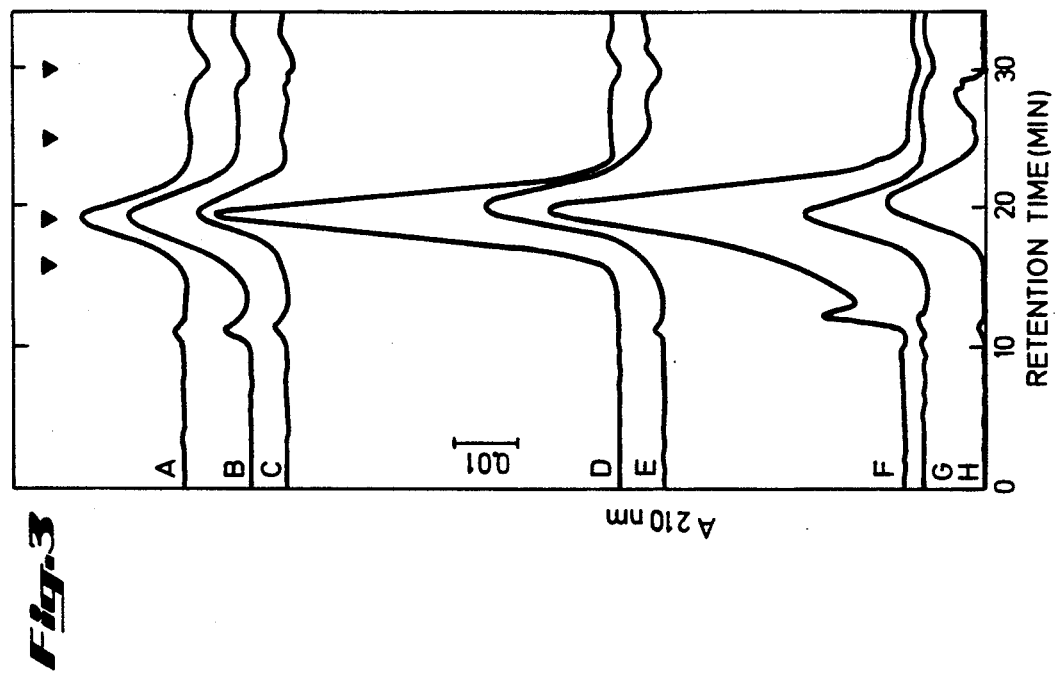
FIG. 3: HPLC of chemically modified heparin on a single 2.7×75 cm column of Fractogel TSK HW-55(S) (Irimura et al., 1983). Elution was accomplished with 0.2M sodium chloride at a flow rate of 0.75 ml/min. During the separation the column was kept at 55° C. by a water jacket. Each sample was dissolved in water (5 ug/ml) and 25 $\mu$l was injected. Patterns a–h indicate the analytical results of derivatized heparins shown in FIG. 1.

Chemical Modifications. Porcine intestinal mucosal heparin was chemically modified as schematically shown by the representative structures in FIG. 1. When the electrophoretic mobilities of these substances in pyridine/acetate buffer on cellulose acetate sheets were compared (FIG. 2), all of the chemical modified heparins migrated more slowly than intact heparin under the electrophoretic condition used. N- and O-desulfated heparins remained at the top of stacking gel and did not stain intensely with Toluidine blue O. The migration distances of the modified heparins were, in order from shortest to longest: N- and O-desulfated heparin, N-acetylated N- and O-desulfated heparin, N-desulfated heparin, N-resulfated N-and O-desulfated heparin, N-acetylated N-desulfated heparin, partially N-desulfated heparin, and carboxy-reduced heparin. High-speed gel-permeation chromatography of these substances was performed as described in Example 1 (FIG. 3). A slight change in the apparent molecular size was observed, probably as a result of detachment and reattachment of the relatively bulky side groups to the heparin chain. Degradation products were not observed in any of the modified heparin preparations as determined by high speed gel permeation chromatography

EXAMPLE 3

HPLC Assay of Heparanase Inhibitory Activities of Chemically Modified Heparins

Figure 4:
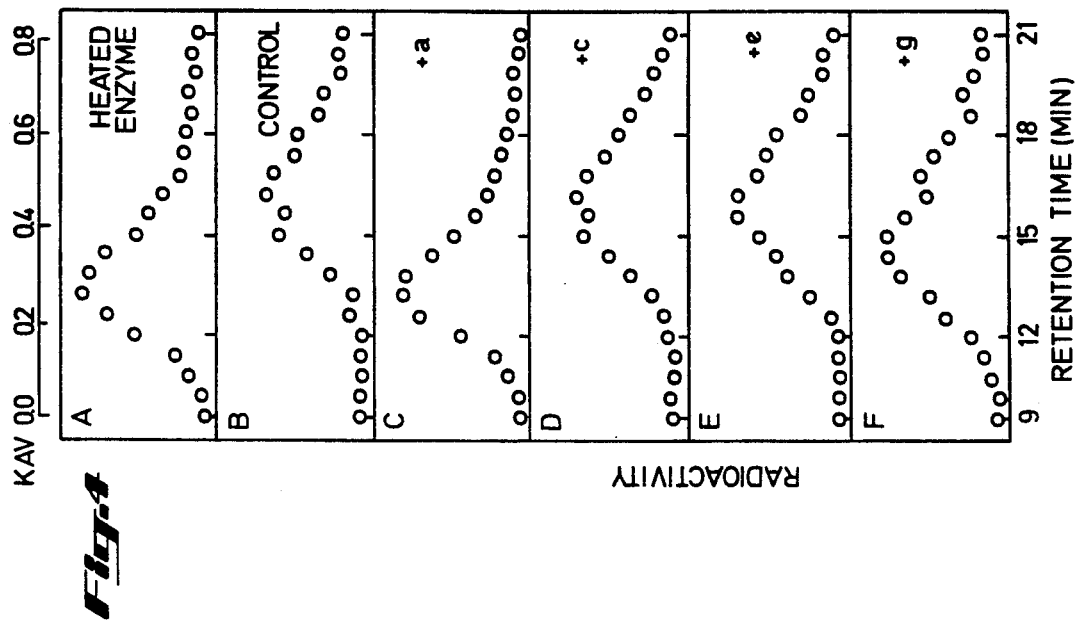
FIG. 4: Results of HPLC assay of B16 melanoma heparanase activity in the presence of chemically modified heparin derivatives. A high-speed gel-permeation chromatography system was equipped with a 0.70×75 cm column of Fractogel TSK-HW55(S). Elution was performed with 0.2M NaCl at a flow rate of 1.0 ml/min at 55° C. Each 0.5-ml fraction corresponding to 30-sec elution was collected, mixed with 3 ml of Hydrofluor and its radioactivity determined. Panel A, $^{14}$C-HS was incubated with heat-inactivated crude heparanase ($10^6$B16-BL6-melanoma cell equivalents) at 37° C. for 6 h, and analyzed. B, same incubation as A except that the enzyme was not heat-inactivated. C, same incubation and analysis as B, but 1 mg/ml of heparin was added to the incubation mixture. D, same incubation and analysis as B, but with 1 mg/ml of completely N-desulfated heparin added to the incubation mixture. E, same incubation and analysis as B, with 1 mg/ml N- and O-desulfated heparin added to the mixture. F, same as B, but with 1 mg/ml of N-resulfated N- and O-desulfated heparin added.

Intact heparin, N-desulfated heparin, N- and O-desulfated heparin, and N-sulfated N- and O-desulfated heparin (4 mg/ml dissolved in water) were mixed with 50 μl of crude heparanase and $^{14}$C-HS as described above. The elution profiles of the radioactivity on high-speed gel-permeation chromatography are shown in FIG. 4. The elution profile of $^{14}$C-HS incubated with heat-inactivated (100° C. for 5 min) heparanase was identical to that of untreated $^{14}$C-HS, which eluted at the position corresponding to an approximate $M_r$ of 34,000. After incubation with heparanase, the average apparent $M_r$ decreased to 6,000. In the presence of heparin, no degradation was observed. N-desulfated heparin or N- and O-desulfated heparin failed to inhibit degradation of HS by heparanase. After N-resulfation of N- and O-desulfated heparin, the heparanase inhibitory activity was partially restored. O-sulfate groups on the 3 or 6 position of glucosamine, as well as on the 2 position of iduronic acid, seem less essential to heparanase inhibition, provided that the amino groups are completely resulfated.

EXAMPLE 4

Solid-phase Assay for Heparanase

Since heparanase is an endoglycosidase that produces relatively large fragments of HS, rapid isolation of the fragmented HS from intact HS is necessary for the quantitative assay. Therefore, HS chains were immobilized at their ends to a solid-phase support, such as small beads. First, $^{35}$S-HS (purified from the subendothelial matrix in cell culture (Wang et al., (1985) Eur. J. Biochem., V 153, pp 125-130) Were immobilized onto Affi-Gel 15, since this HS preparation contained amino acid residues at its reducing terminal end. With use of this substate, however, the proportion of $^{35}$S-labeled materials released from the beads by crude heparanase was negligible, and this method was not found likely to be useful. Next, chemically labeled and modified HS was immobilized on beads. Deacetylation of HS was achieved by hydrazinolysis. Lower temperatures and shorter reaction times than the usual hydrazinolysis reactions of glycoproteins (Fukuda et al., (1976) J. Biochem., V 80, pp 1223-1232); Irimura et al., (1981) Biochem, V 20, pp 560-566) were chosen because of possible cleavage of uronosylglucosaminide through these amino groups. Resultant N-deacetylated heparin was labeled by N-$^{14}$C- or $^3$H-acetylation. It appeared to be important to subsequently block all free amino groups by acetylation with non-radioactive acetic anhydride, which was done. Radio-labeled HS was aminated exclusively at its reducing terminal by reductive amination, and coupled to Affi-Gel 15 linkage under alkaline conditions. The proportion of labeled HS coupled to agarose beads fluctuated between 50 and 80% calculated from the amount of material used for the amination reaction. As a heparanase substrate, partially N-desulfated and N- $^3$H- or $^{14}$C-acetylated HS are also as useful as deacetylated and reacetylated HS. Partial N-desulfation of HS was achieved by the same reaction conditions used for partial N-desulfation of heparin described under Materials and Methods.

EXAMPLE 5

Figure 5:
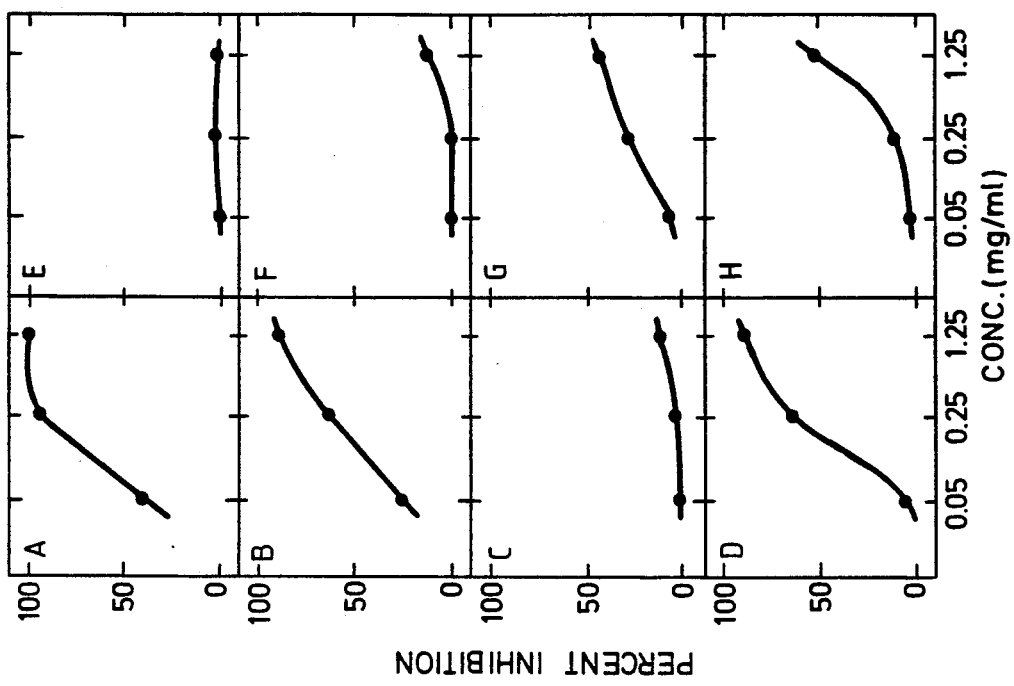
FIG. 5: Inhibitory activities of chemically modified heparins on release of $^3$H-acetylated HS fragments by metastatic B16 melanoma heparanase. The measurements were performed by incubating B16-BL6 melanoma heparanase. The measurements were performed by incubating B16-BL6 melanoma cell lysates equivalent to $10^6$ cells with a suspension of $^3$H-HS-agarose beads prepared by partial N-desulfation and $^3$H-acetylation (approximately 20% suspension), and various concentrations of heparanase inhibitors at 37° C. for 24 hr with gentle mixing. Panels a–h indicate the results using the 8 different chemically modified heparins as indicated in FIGS. 1 and 2. The inhibitory activities are indicated by the percent release of HS fragments compared to the release without added inhibitors.

Heparanase Inhibition by Chemically Modified Heparins as Measured by a Solid-phase Assay The dose response curves of the inhibitory effects of chemically modified heparins are shown in FIG. 5. The use of i) intact, ii) N-desulfated, iii) N- and O-desulfated and iv) N-resulfated, N- and O-desulfated heparin produced results consistent with those of the HPLC assay. N-desulfated and N- and O-desulfated heparin failed to how any inhibitory activity, whereas partial restoration of activity was obtained by the addition of sulfamino groups (FIG. 5g). Interestingly, when the exposed amino groups formed by N-desulfation were acetylated, heparanase inhibitory activity was partially restored (FIG. 5d). N-Acetylation of N- and O-desulfated heparin did not, however, restore the inhibitory activity (FIG. 5f). These results indicated that sulfamino groups, although they affected heparanase inhibition, were not essential for it. Removal of sulfamino groups, but with intact O-sulfate groups of heparin resulted in inhibitory activity, provided that the exposed amino groups are blocked by acetylation. Carboxy-reduced heparin was shown to possess weaker inhibitory activity than heparin, which indicated that heparin carboxy groups were necessary but not essential, for the full inhibitory activity. Similar observations have been described concerning heparin's stimulatory activity on the growth of smooth muscle cells (Castellot et al., (1984) J. Cell. Physiol., V 120, pp 315-320).

EXAMPLE 6

Modified Heparins as Anticoagulants

Anticoagulation activities of N-acetylated N-desulfated heparin, N-resulfated N- and O-desulfated heparin, and carboxyl-reduced heparin were measured by the USP standard assay. The anticoagulation activities of these three compounds were each less than 1% of the anticoagulation activity of unmodified heparin.

EXAMPLE 7

Effects of Modified Heparins on Experimental Blood-borne Lung Colonization of B16 Melanoma in Mice As shown in Table 1, the number of visible melanoma colonies in lung 20 days after the injection of the tumor cells was significantly reduced by preincubation of the cells with intact or chemically modified heparin. The effect of intact heparin was greater, probably because additional factors such as inhibition of melanoma-induced platelet aggregation were involved. Since these three chemically modified heparins do not possess anticoagulation activity, the inhibition of melanoma lung colonization appeared to be due to inhibition of melanoma heparanase.

TABLE 1

THE EFFECTS OF CHEMICALLY-MODIFIED HEPARINS ON BLOOD-BORNE LUNG COLONIZATION OF B16-BL6 MELANOMA CELLS IN MICE

| Treatment[a] | Exp 1 (9 mice/group) Number of colonies (median) | Exp 2 (9 mice/group) Number of colonies (median) |
|---|---|---|
| None | 8, 20, 28, 33, 75, 85, 106, 116, 193, (75) | 0, 1, 26, 48, 75, 163, 193, 200+, 200+, (75) |
| Heparin | 0, 1, 8, 9, 16, 18, 21, 82, 174, (16) | 0, 0, 0, 0, 0, 1, 1, 2, 12, (0) |
| N-acetylated-N-desulfated heparin | 11, 19, 22, 23, 43, 89, 109, 199, (43) | 0, 1, 2, 3, 5, 5, 25, 37, 200+, (5) |
| N-resulfated-N-, O-desulfated heparin | | 0, 0, 2, 5, 8, 13, 20, 90, 200+, (8) |
| Carboxy-reduced heparin | 0, 15, 25, 25, 39, 36, 45, 46, 53, (29) | 7, 13, 42, 49, 51, 55, 58, 89, 120, (51) |

[a]The cells were incubated with chemically modified heparins (500 ug/ml) at 4~ C. for 2 hr before injection.

EXAMPLE 8

Effects of Modified Heparins on the Degradation of Lung Capillary Endothelial Matrix by Melanoma Cells in Vitro Effects of chemically modified heparins on the release of $^{35}$S-labeled polysaccharides from the extra-cellular matrix of mouse lung endothelial cells were studied in vitro. The endothelial cells isolated from mouse lung capillary were grown in the presence of $^{35}$S-sulfate, and the extracellular matrix-like material was isolated on multiwell plastic tissue culture plates by hypotonic lysis of the cells. The matrices (1 cm diameter) were incubated with mouse B16-BL6 melanoma at 37° C. for 18 hours. The released radioactivity was counted.

Figure 6:
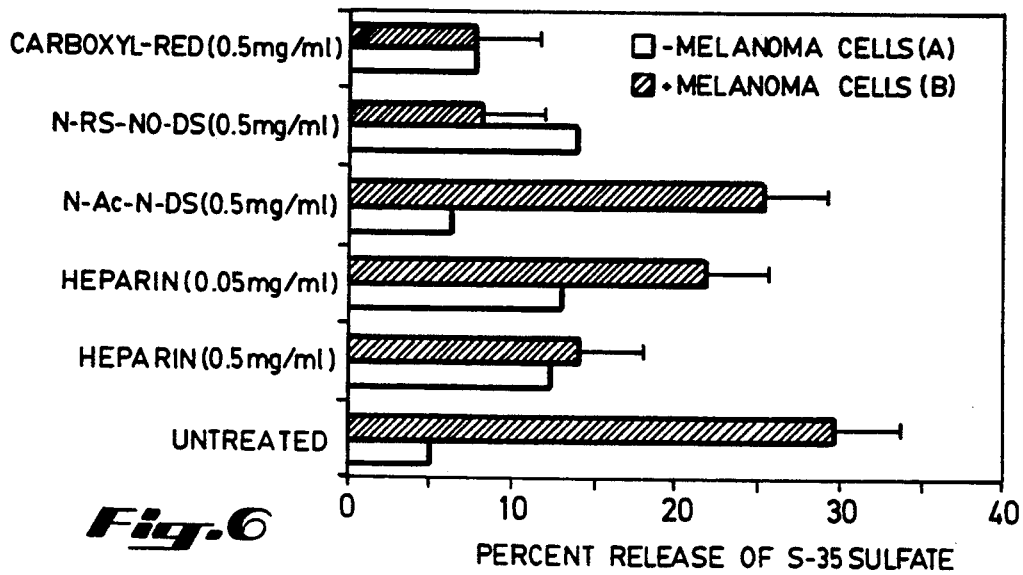
FIG. 6: Effects of chemically modified heparins on the release of $^{35}$S labeled substances from the extracellular matrix of mouse lung capillary endothelial cells in vitro. Heparin and some chemically modified heparins induced non-enzymatic release of $^{35}$S labeled materials in the absence of B16 melanoma cells, while they inhibited the degradation of these macro molecules caused by B16 melanoma cells. (See: Nakajima et al., Science 220:611–613, 1983, for the methods.)

As shown in the FIG. 6, N-resulfated- N-, O-desulfated heparin and carboxyl-reduced heparin effectively blocked the degradation of sulfated molecules, most likely heparan sulfate proteoglycans, by melanoma cells. Heparin apparently induced spontaneous release of $^{35}$S labeled macromolecules, while such effects were minimal with modified heparins.

EXAMPLE 9

Effects of Modified Heparins on the Growth of B16 Melanoma Cells in Tissue Culture In order to assess a possibility that the effects of modified heparins on the blood-borne lung colonization of B16 melanoma cells were due to their direct toxic effects on the cells, the growth of B16 melanoma in the presence or absence of modified heparins were examined in vitro. B16-BL6 melanoma cells were seeded in multiwell tissue culture plates at a density 10,000 per each 1 cm well in the presence or absence of 5% fetal bovine serum. Six hours later, modified heparins were added, then 24 hours later, $^3$H thymidine was added to a final concentration 5 uCi/ml. After further 24 hour incubation, trichloroacetic acid-insoluble materials were collected, dissolved in 1M sodium hydroxide solution, neutralized and counted on a liquid scintillation counter.

Figure 7:
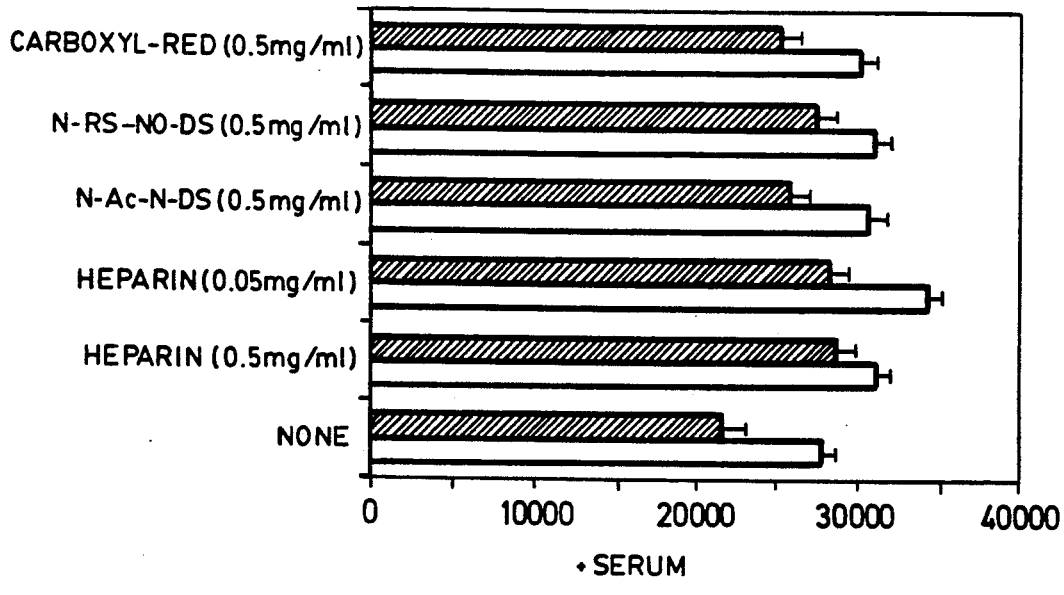
FIG. 7: Effects of chemically modified heparins on the incorporation of $^3$H-thymidine to B16-BL6 melanoma cells grown in tissue culture. (See: Irimura et al., (1981) Cancer Res. 41:3411–3418, for the methods.)

FIG. 7 shows typical data demonstrating that there are no significant effects on the incorporation of $^3$H-thymidine to B16 cells shown by unmodified heparin N-acetylated-N-desulfated heparin, N-resulfated- N-, O-desulfated heparin or carboxyl-reduced heparin. These data indicated that the in vivo effects of these compounds were due to the influence on the tumor cell-host interactions.

EXAMPLE 10

Figure 8A:
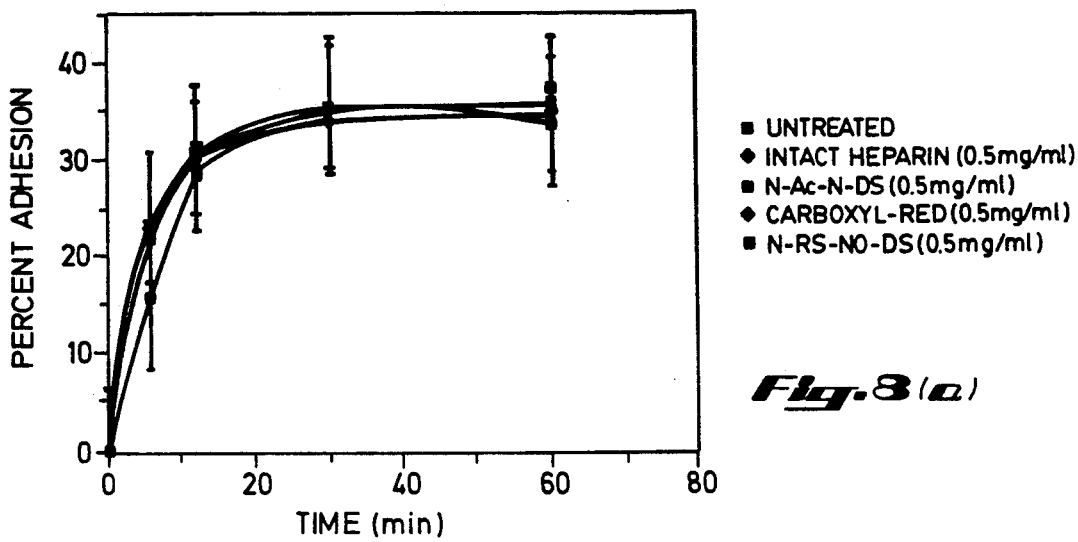
FIG. 8(a) B16 melanoma cells were pretreated with modified heparins at room temperature for 2 hrs, and the adhesion assays were performed in the continuous presence of these compounds at 37° C.
Figure 8B:
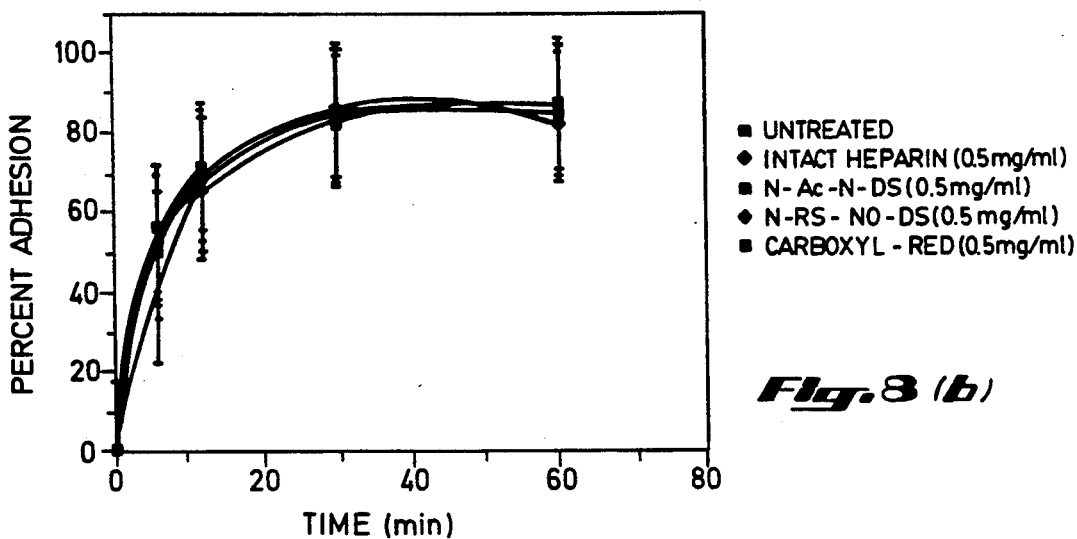
FIG. 8(b) Endothelial cells were pretreated with modified heparins at 37° C. for 2 hrs, then adhesion assays were performed. (See Nicolson and Custead, (1985) Cancer Res. 45:331–336, for the methods FIG. 9: Effects of modified heparins on the adhesion of B16-F10 melanoma cells to the syngenic mouse lung tissues in vitro. Primary organ cultures of minced mouse lung tissues were mixed with melanoma cell suspensions and incubated at 37° C. under gentle gyration. The attached melanoma cells to the lung tissues were histologically quantitated after sectioning. (See Nicolson et al., (1985) Invasion Metastasis, 5:144–158, for detailed methods.)

Effects of Modified Heparins on the Adhesion of B16 Melanoma Cells to the Monolayer and to the Extracellular Matrix of Lung Capillary Endothelial Cells One of the most critical steps in the tumor cell-microvascular endothelium interaction during metastatic lung colonization of melanoma cells is the adhesive interaction of melanoma cells with endothelial cells. The effects of modified heparins on the adhesion of B16 melanoma to the cell monolayer and to the extracellular matrix of lung capillary endothelial cells were studied in vitro. The endothelial cells were grown in tissue culture and the extracellular matrices were isolated as described in Example 8. FIG. 8(a) shows the time course of the adhesion of B16-BL6 cells previously treated with modified heparins to the monolayer of endothelial cells, in the continuous presence of modified heparins. None of these compounds, including intact heparin, significantly altered the time course of the adhesion of B16-BL6 cells to the endothelial cell monolayer. Prior treatment of endothelial cells for 2 hrs with these compounds also resulted in no significant alteration in the adhesion (FIG. 8(b)).

EXAMPLE 11

Effects of Modified Heparins on Adhesion to and Invasion of Organ-Cultured Lung Tissues by Melanoma Cells in Vitro The effects of these glycosaminoglycan derivates on organ-specific adhesion and invasion of B16 melanoma cells were studied by using primary organ culture techniques in vitro. Minced lung tissues (0.5-1.0 cubic mm) from C57BL/6 mice were placed in glass vials and incubated in HEPES-buffered Dulbecco's modified minimum essential media containing 10% fetal bovine serum and 50 ug/ml gentamycin under continuous gyration at 66 rpm. After the medium was changed to a fresh medium without gentamycin, B16-F10 melanoma cells were added at a final concentration of 100,000/ml with or without various modified heparins. After various incubation times, the tissues were fixed in buffered formalin and processed for light microscopy. The adhesion and invasion of the tumor cells were examined on 4 mm thick sections stained with hematoxylin and eosin.

Figure 9:
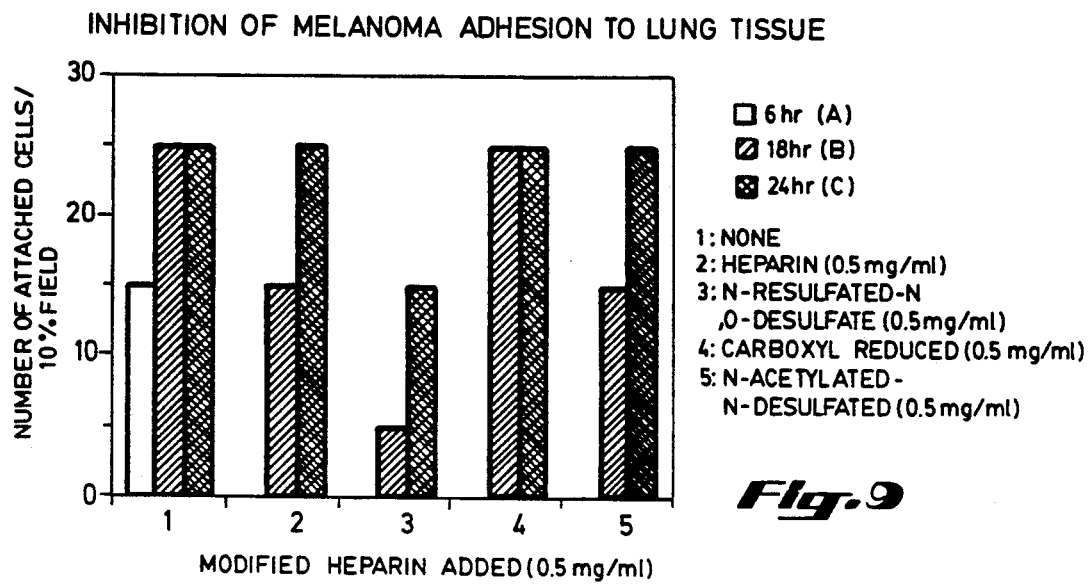
Figure 10:
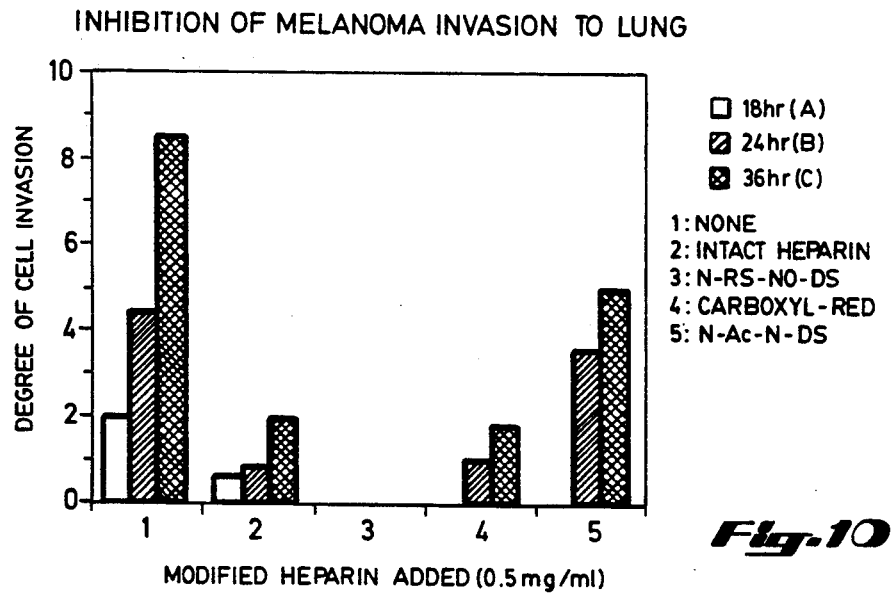
FIG. 10: Effects of modified heparins on the B16-F10 melanoma cell-invasion of isolated mouse lung tissues in vitro. The experimental conditions were the same as the adhesion experiments. The invaded cells were counted on 4 $\mu$m sections under a light microscope. (See Nicolson et al., (1985) Invasion Metastasis, 5:144–158, for detailed methods.)

As shown in FIG. 9, the number of melanoma cells attaching to the surface of minced lung tissues was significantly affected by the compounds at the early stages of incubation (6 hrs), but little effect was present after 18 hrs Heparin and modified heparins inhibited invasion of B16 melanoma cells to the lung tissues, as shown in FIG. 10. These data clearly indicated that these compounds possess capacity to block lung invasion of B16 melanoma cells.

EXAMPLE 12

In Vivo Inhibition by Heparin Derivatives of Metastatic Colonization by Melanoma Cells Chemically modified heparins were tested in mice as inhibitors of blood-borne lung colonization by melanoma cells. Male C57BL/6 mice 4 to 6 weeks old were obtained from Charles River, Inc. and quarantined for 2 weeks. The mice were intravenously inoculated with $5 \times 10^4$ B16-BL melanoma cells. Treated mice were intravenously injected with 0.1 ml each of heparin or chemically modified heparin (5.0 mg/ml) 4 hr before and 20 hr after inoculation with the melanoma cells. The chemically modified heparins used were: N-acetylated N-desulfated heparin; carboxyl-reduced heparin; and N-resulfated N, O-desulfated heparin.

Mice were killed 20 days after tumor inoculation and autopsied. The numbers of pulmonary tumor colonies were counted after the lungs were perfused via the trachea with 4% formalin in Dulbecco's phosphate-buffered saline. The results of these manipulations are shown in Table 2. As may be seen in Table 2, heparin as well as the glycosaminoglycan derivatives substantially devoid of anticoagulation activity all impeded the establishment of metastatic tumor colonies in the lungs. Although heparin itself inhibited formation of lung metastases, the carboxyl-reduced heparin was most effective in this particular manner.

TABLE 2

EFFECTS OF CHEMICALLY MODIFIED HEPARINES ON BLOOD-BORNE LUNG COLONIZATION OF B16 MELANOMA CELLS IN SYNGENEIC MICE

| Treatment | Number of lung colonies | Median |
|---|---|---|
| None | 3, >150, >150, >150, >150, >150 | >150 |
| Heparin | 19, 20, 29, 30, 40, 99, 100 | 30 |
| N-acetylated N-desulfated heparin | 4, 26, 28, 50, 60, >150, >150, >150 | 60 |
| Carboxyl-reduced heparin | 0, 0, 1, 3, 6, 6, 60, 61 | 6 |
| N-resulfated, N,O-desulfated heparin | 0, 1, 28, 28, 30, 36, 38, >150, >150 | 36 |

EXAMPLE 13

In Vivo Inhibition by Heparin Derivatives of Metastatic Colonization by Mammary Carcinoma Cells Inbred 8-week-old female Fischer (F344/CDL) rats were supplied by the Charles River Breeding Laboratories (Kingston, N.Y.). Animals were quarantined for 7 days before use and feed standard rodent chow and unchlorinated spring water ad libitum. They were maintained under guidelines set forth by the University of Texas M. D. Anderson Cancer Center and the Institute of Laboratory Animal Resources, National Research Council. As a source of breast carcinoma cells, a cloned line of the 13762NF rat mammary adenocarcinoma MTF7 (Neri, A., Welch, D. R., Kawaguchi, T., Nicolson, G. L. *J. Natl. Cancer Inst.*, 68:507–517, 1982) was used. The cells grown at 37° C. in an atmosphere of 5% $CO_2$ in humidified air in an 1:1 mixture of Dulbecco's modified minimum essential media and Ham's F12 media containing 10% fetal bovine serum and no antibiotics in 100 mm-diam. tissue culture plates.

The cells used in this study were in exponential growth phase and were from passages 14 to 20 in vitro and were free of mycoplasma and viral contamination. Cells were detached from tissue culture plates by brief treatment with 2 mM EDTA and 0.25% trypsin, rinsed with media (1:1 mixture of Dulbecco's modified minimum essential media and Ham's F12 media) containing 10% fetal bovine serum and with serum-free media, and then suspended in serum-free media.

Unmodified and chemically modified heparins (Irimura, T., Nakajima, M., Nicolson, G. L. Biochemistry, 25:5322–528, 1986) were dissolved in Dulbecco's phosphate buffered saline at a concentration 10 mg/ml. Rats (9 per group) were injected i.v. (lateral tail vein) with 0.1 ml of 10 mg/ml solution of heparin, N-acetylated-N-desulfated heparin, or carboxyl-reduced heparin. Eight hours later, the same rats were injected i.v. with $5 \times 10^4$ MTF7 mammary carcinoma cells suspended in 0.2 ml serum-free media. Sixteen hours after injections of carcinoma cells, rats were treated with unmodified or chemically modified heparin at the same dose as the previous treatment 8 hours prior to the injection of carcinoma cells.

Rats were killed 30 days after the initial injection of carcinoma cells and examined for the number of lung tumor colonies, that should represent the degree of metastatic spread of mammary carcinoma cells. The results are shown in Table 3. Although heparin itself was most effective in this experiment, the N-acetylated, N-desulfated and carboxyl-reduced heparins were also effective. The latter two derivatives are of course depleted in anticoagulation activity.

TABLE 3

EFFECT OF MODIFIED HEPARINS ON EXPERIMENTAL METASTASIS OF RAT MAMMARY ADENOCARCINOMA MTF7

| Heparin Derivative | Lung Metastases per rat | |
|---|---|---|
| | Number | Median No. |
| None | 45, 47, 56, 67, 68, 71, 73, 73, 79 | 68 |
| Heparin | 0, 0, 0, 5, 9, 10, 27, 33, 35 | 9 |
| N-Acetylated-N-desulfated heparin | 8, 18, 20, 23, 29, 32, 44, 56, 62 | 29 |
| Carboxyl-reduced heparin | 10, 11, 14, 19, 25, 26, 39 45, 52 | 25 |

Changes may be made in the operation and arrangement of the various elements, substances and procedures described herein without departing from the concept and scope of the invention as defined in the following claims.

What is claimed is:

1. A method for impeding melanoma or carcinoma cell metastasis in a host consisting essentially of:
   providing a heparin derivative which is substantially devoid of anticoagulation activity and is an effective inhibitor of heparanase activity; and
   parenterally administering an antimetastatically effective amount of the heparin derivative to a melanoma or carcinoma cell host.

2. A method for inhibiting the invasiveness of melanoma or carcinoma cells in a host, the method consisting essentially of inhibiting heparanase activity of said cells by administering to a host an antimetastatically effective amount of heparin derivative substantially devoid of anticoagulant activity but with heparanase inhibitory activity.

3. The method of claim 1 or 2 wherein the antimetastatically effective amount is between about 30 mg/day and 250 mg/day.

4. The method of claim 1 or 2 wherein the antimetastatically effective amount is between about 30 mg/day and 100 mg/day.

5. A method for inhibiting the spread of metastatic melanoma or carcinoma cells subsequent to or simultaneous with surgical removal of a primary melanoma or carcinoma from a host, the method consisting essentially of parenterally administering to said host an antimetastatically effective amount of a heparin derivative substantially without anticoagulant activity but with heparanase inhibitory activity.

6. The method of claims 1, 2 or 5 wherein the heparin derivative comprises sulfamino or O-sulfate groups.

7. The method of claim 1, 2 or 5 wherein the heparin derivative has a molecular weight between about 1,000 and about 15,000.

8. The method of claim 1, 2 or 5 wherein the heparin derivative has a molecular weight between about 10,000 and about 12,500.

9. The method of claim 1, 2 or 5 wherein the carcinoma is a mammary carcinoma.

10. The method of claim 1, 2 or 5 wherein the heparin derivative has the formula:

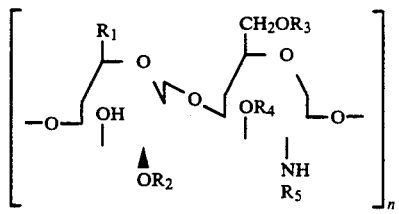

where
$R_1$ is —COOH or —CH$_2$OH and the configuration of the carbon atom to which $R_1$ is bound is D or L;
$R_2$ is —H or —SO$_3^-$;
$R_3$ is —H or —SO$_3^-$;
$R_4$ is —H or —SO$_3^-$;
$R_5$ is —H, —SO$_3^-$ or —CO—CH$_3$;
n is 3 to 30; and
each terminal monomeric unit is a monomeric repeating unit with a terminal oxygen atom being bound to a blocking group.

11. The method of claim 1, 2 or 5 wherein the heparin derivative has the formula:

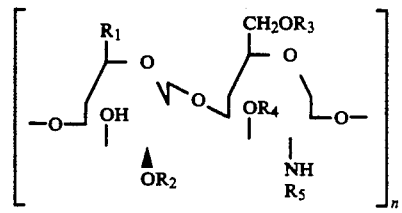

where
$R_1$ is —COOH or —CH$_2$OH and the configuration of the carbon atom to which $R_1$ is bound is D or L;
$R_2$ is —H or —SO$_3^-$;
$R_3$ is —H or —SO$_3^-$;
$R_4$ is —H or —SO$_3^-$;
$R_5$ is —SO$_3^-$ or —CO—CH$_3$; and
n = 3–30;
provided that: when $R_1$ is —CH$_2$OH, at least 50% of $R_2$, $R_3$ and $R_5$ is —SO$_3^-$;
when $R_1$ is —COOH and $R_2$, $R_3$ and $R_4$ are —H, $R_5$ is —SO$_3^-$;
when $R_1$ is —COOH and at least 50% of $R_2$, $R_3$ and $R_4$ is —SO$_3^-$, $R_5$ is —CO—CH$_3$; and
each terminal monomeric unit is a monomeric repeating unit having a terminal oxygen atom bound to a blocking group.

* * * * *

UNITED STATES PATENT AND TRADEMARK OFFICE
CERTIFICATE OF CORRECTION

PATENT NO. : 5,262,403
DATED : November 16, 1993
INVENTOR(S) : Garth L. Nicholson, Tatsuro Irimura, and Motowo Nakajima It is certified that error appears in the above-identified patent and that said Letters Patent is hereby corrected as shown below:

Please correct the figures in claims 10 and 11 as follows:

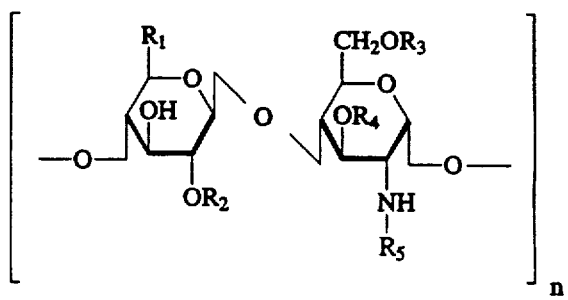

Signed and Sealed this

Twelfth Day of July, 1994

Attest:

BRUCE LEHMAN

Attesting Officer            Commissioner of Patents and Trademarks

UNITED STATES PATENT AND TRADEMARK OFFICE
CERTIFICATE OF CORRECTION

PATENT NO. : 5,262,403

DATED : November 16, 1993

INVENTOR(S) : Garth L. Nicolson, Tatsuro Irimura, and Motowo Nakajima

It is certified that error appears in the above-identified patent and that said Letters Patent is hereby corrected as shown below:

In line 1 of column 1, add the sentence -

--The United States government has rights in the present patent due to research support by federal grant number R35 CA44352.

Signed and Sealed this

Twenty-eight Day of March, 1995

Attest:

BRUCE LEHMAN

Attesting Officer     Commissioner of Patents and Trademarks